United States Patent [19]

Lennon

[11] Patent Number: 5,905,163
[45] Date of Patent: *May 18, 1999

[54] METHOD FOR PREPARING AMINOMETHYLPHOSPHONATE DERIVATIVES VIA HYDROGENATION OF CYANOPHOSPHONATE DERIVATIVES

[75] Inventor: Patrick J. Lennon, Webster Grove, Mo.

[73] Assignee: Monsanto Company, St. Louis, Mo.

[*] Notice: This patent is subject to a terminal disclaimer.

[21] Appl. No.: 08/996,948

[22] Filed: Dec. 23, 1997

Related U.S. Application Data

[60] Provisional application No. 60/034,515, Dec. 30, 1996.
[51] Int. Cl.$^6$ .................. C07F 9/40; C07F 9/38
[52] U.S. Cl. .............. 558/87; 423/302; 558/145; 558/166; 558/167; 562/16
[58] Field of Search .............. 423/302; 558/87, 558/145, 166, 167; 562/16

[56] References Cited

U.S. PATENT DOCUMENTS

| | | |
|---|---|---|
| 2,402,703 | 6/1946 | Woodstock . |
| 2,702,299 | 2/1955 | Harris . |
| 3,432,277 | 3/1969 | Roesky ...................................... 23/357 |
| 3,812,221 | 5/1974 | Braden et al. ........................... 260/968 |
| 4,221,583 | 9/1980 | Gaertner et al. . |
| 4,568,432 | 2/1986 | Rogers . |

FOREIGN PATENT DOCUMENTS

| | | | |
|---|---|---|---|
| 300 936 | 9/1992 | Germany ........................... C07F 9/40 |
| 96/15135 | 5/1996 | WIPO . |

OTHER PUBLICATIONS

Abstract–Database WPI, Section Ch, Week 7615, Derwent Publications Ltd., London, GB; Class B04, AN 76–27192X, XP002061354 & JP 51 023 225 A (Nippon Chem. Ind. Co. Ltd.), Feb. 24, 1976.

Blanchard, J. "Préparation d–acides beta–amino–ethyl–phosphoniques" *Tetrahedron,m*; vol. 32, No. 4, 1976, Oxford GB, pp. 455–459, XP002061374.

Chemical Abstracts, vol. 093, No. 12, Sep. 22, 1980, Columbus, Ohio, US; abstract no. 123612, Zhurba, Y.I. et al. "Increase in the stability of silver complexes in the process of simultaneous developing and fixing" and ZH NAUCHN, PIRKL. FOTOGR. KINEMATOGR. (ZNPFAG, 00444561); 80; vol. 25(3); pp. 182–185, VSES. GOS. NAUCHNO–ISSLED.PROEKTN. INST. KHIM.–FOTOGR. PROM., Moscow; USSR; XP002061352.

Dyatkina, N. et al. Synthesis and antiviral activity of some fluorinated nucleotide derivativers: NUCLEOSIDES NUCLEOTIDES (NUNUD5, 07328311); 94; col. 13 (1–3); pp. 325–337, ENGELHARDT INST. MOL. BIOL.; Mowcow; 117984. Russia XP002061348.

Kashemirov, B.A. "(E)–(Hydroxyimino)(hydroxymethoxyphosphinyl)acetic acid: Synthesis and pH dependent fragmentation," *Tetrahedron Letters*, vol. 36, No. 52, 1995, Oxford GB, pp. 9437–9440; XP002061351.

Albrecht et al., "Reaction of the Two–Component System Trialkyl Phosphite/Carbon Tetrachloride with Nucleophiles 3. Reaction in Presence of Trialkylammonium Salts," *Z. anorg. allg. Chem.* 552: 132–146 (1987) and English language translation.

Kashemirov et al., "Troika Acids: Synthesis, Structure, and Fragmentation Pathways of Novel α–(Hydroxyimino)phosphonacetic Acids," *J. Am. Chem. Soc.* 117:7285–7286 (1995).

Shioiri et al., "Reaction of Diethyl Phosphorocyanidate(DEPC) with Carboxylic Acids. A New Synthesis of Carboxylic Esters and Amides," *Tetrahedron* 32(18):2211–2217 (1976).

Tung et al., "A New Method for the Preparation of O,O'–Dialkylphosphoryl Cyanides," *Hua Hsueh Hsueh Pao (Acta Chimica Sinica)* 31(3): 199–202 (1965).

*Primary Examiner*—Michael G. Ambrose
*Attorney, Agent, or Firm*—Arnold, White & Durkee

[57] ABSTRACT

A novel process for preparing aminomethylphosphonate derivatives involves the hydrogenation of cyanophosphonate derivatives in the presence of a catalyst to produce aminomethylphosphonate derivatives.

42 Claims, No Drawings

METHOD FOR PREPARING AMINOMETHYLPHOSPHONATE DERIVATIVES VIA HYDROGENATION OF CYANOPHOSPHONATE DERIVATIVES

This application claims the benefit of provisional application Ser. No. 60/034,515, filed Dec. 30, 1996.

BACKGROUND OF THE INVENTION

Organophosphorus compounds have numerous and varied applications, for example, in herbicides, insecticides, fertilizers, flame retardants and plasticizers and as precursors for the synthesis of other organophosphorus compounds. Aminomethylphosphonates are of particular interest due to their versatility in synthetic pathways and a wide range of chemistries can extend from both the phosphorus and amino moieties. In particular, aminomethylphosphonates are important precursors in the synthesis of N-phosphonomethylglycine, a highly effective commercial herbicide (available under the trade name Roundup™) useful for the control of a large variety of weeds.

There exists a need for organophosphorus compounds and methods for their preparation to enable the preparation of organophosphorus materials with a variety of beneficial uses. There is a further need for such methods and compounds that are economical and environmentally safe.

SUMMARY OF THE INVENTION

This invention relates to a novel method for preparing aminomethylphosphonate derivatives of the formula:

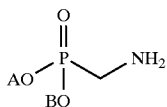

wherein A and B are the same or different, and are hydrogen, a cation or an ester group such as an alkyl group, an aryl group or an arylalkyl group. The aminomethylphosphonate derivative can also be an anhydride of a phosphonate such as an aminomethylphosphonate, an anhydride of a phosphate group or an anhydride of a mixed phosphonate-phosphate.

The inventive method for preparing an aminomethylphosphonate derivative involves contacting a cyanophosphonate derivative with hydrogen in the presence of a suitable catalyst.

The processes and compositions according to the invention offer significant advantages in that they provide a novel, economic route to synthesize aminomethylphosphonate derivatives having an improved environmental impact over conventional processes using halogen-containing phosphorus starting materials.

DESCRIPTION OF ILLUSTRATIVE EMBODIMENTS

The invention is broadly directed to a method for preparing aminomethylphosphonate derivatives of the formula:

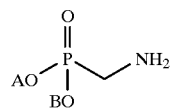

wherein A and B are the same or different, and are hydrogen, a cation or an ester group such as an alkyl group, an aryl group, or an arylalkyl group via hydrogenation of a cyanophosphonate derivative in the presence of a suitable catalyst. The aminomethyl phosphonate derivative can also be an anhydride of a phosphonate such as an aminomethylphosphonate, an anhydride of a phosphate group or an anhydride of a mixed phosphonate-phosphate.

The aminomethylphosphonate derivative is prepared by contacting a cyanophosphonate derivative, hydrogen and a suitable catalyst in a reaction mixture under sufficient conditions to produce an aminomethylphosphonate derivative. In a preferred embodiment, the contacting step involves charging a reaction vessel with cyanophosphonate derivative, hydrogen, and a suitable catalyst and preferably also a solvent. The contacting step is performed under conditions sufficient for the preparation of aminomethylphosphonate derivatives, preferably at a temperature in the range of about 10° C. to about 70° C., more preferably in the range of about 20° C. to about 50° C. and most preferably in the range of about 20° C. to about 40° C. The hydrogenation step is performed for a period of time sufficient for the preparation of an aminomethylphosphonate derivative. Preferably, the hydrogenation step is performed for an amount of time between about 0.1 and about 24 hours, and more preferably for between about 0.1 and about 12 hours.

The pH of the reaction solution upon completion of the contacting step will affect the protonation state of the aminomethylphosphonate product. For example, high pH values will favor deprotonation of both the amine and the phosphonic acid moieties, while low pH values will favor protonation.

The cyanophosphonate derivative is generally any cyanophosphonate derivative suitable for participating in the inventive method to prepare an aminomethylphosphonate derivative. Generally, the cyanophosphonate derivative can be a cyanophosphonate disalt, a cyanophosphonate monosalt monoester, a cyanophosphonate diester, a cyanophosphonate monosalt monoacid, a cyanophosphonate monoacid monoester or cyanophosphonic acid. The cyanophosphonate derivative can also be a cyclic cyanophosphonate anhydride, a linear or polymeric cyanophosphonate anhydride, a mixed linear or polymeric cyanophosphonate-phosphate anhydride, a mixed linear or polymeric cyclic cyanophosphonate-phosphate anhydride or a mixed cyclic cyanophosphonatephosphate anhydride. The terminal P-O moieties in these cyanophosphonate anhydrides can be neutral, protonated, anionic or esterified.

Cyanophosphonate derivatives suitable for the method according to the invention include those described in and prepared by the methods described in co-pending U.S. patent applications Ser. No. 08/996,945 entitled "Method for Preparing Cyanophosphonate Derivatives from Pyrophosphate or Polyphosphate Esters and Cyanide" by Patrick J. Lennon and Sergey G. Vulfson, filed Dec. 23, 1997; Ser. No. 08/996,949 entitled "Method for Preparing Cyanophosphonate Derivatives from Phosphoric Anhydride and Cyanide" by Patrick J. Lennon and Sergey G. Vulfson, filed Dec. 23, 1997; Ser. No. 08/997,339 entitled "Novel Cyanophosphonate Derivatives and Method for Their Preparation" by Patrick J. Lennon and Sergey G. Vulfson, filed Dec. 23, 1997; Ser. No. 08/996,946 entitled "Cyanophosphorus Compounds and Their Preparation" by Patrick J. Lennon and Sergey G. Vulfson, filed Dec. 23, 1997; and Ser. No. 08/996,947 entitled "Method for Preparing Cyanophosphonate Derivatives from Phosphate Esters and Cyanide" by Patrick J. Lennon and Sergey G. Vulfson, filed Dec. 23, 1997, each of which is incorporated herein by reference. The material to be hydrogenated may be a single cyanophosphonate derivative or mixture of cyanophosphonate derivatives, including mixtures as found in the product solutions or portions of the product solutions from methods disclosed in the above incorporated patent applications.

In a preferred embodiment, the cyanophosphonate derivative can be one or more of disodium cyanophosphonate, dipotassium cyanophosphonate, dilithium cyanophosphonate, bis(2-hydroxyethylammonium) cyanophosphonate, bis(ammonium)cyanophosphonate, bis(isopropyiammonium)cyanophosphonate, mono(isopropylammonium)cyanophosphonate, bis(dimethylammonium)cyanophosphonate, bis(trimethylsulfonium) cyanophosphonate, bis(dicyclohexylammonium)cyanophosphonate, cyanophosphonic acid, sodium hydrogen cyanophosphonate, potassium hydrogen cyanophosphonate, lithium hydrogen cyanophosphonate, methyl cyanophosphonic acid, ethyl cyanophosphonic acid, sodium methyl cyanophosphonate, sodium ethyl cyanophosphonate, potassium methyl cyanophosphonate, potassium ethyl cyanophosphonate, lithium methyl cyanophosphonate, lithium ethyl cyanophosphonate, dimethylcyanophosphonate, diethylcyanophosphonate, sodium benzyl cyanophosphonate, potassium benzyl cyanophosphonate, lithium benzyl cyanophosphonate, lithium 5-methyl-2-nitrophenylcyanophosphonate, lithium p-nitrophenyl cyanophosphonate and lithium 2,6-dichlorophenyl cyanophosphonate.

In another preferred embodiment, the cyanophosphonate derivative can be monocyanopyrophosphate, dicyanopyrophosphate, dicyanotripolyphosphate, dicyanotetrapolyphosphate, monocyanotetrapolyphosphate, monocyanopentapolyphosphate, cyanophosphonate cyclotrimer or cyanophosphate cyclotetramer.

The solvent can be any material that enhances the solubility of reactants or promotes the formation of the desired products. In a preferred embodiment, the solvent is water, acetic acid, an alcohol, dimethylacetamide, an anhydride, e.g., acetic anhydride, an amide, sulfolane or mixtures thereof.

Hydrogen pressure can be maintained at a level suitable for the formation of an aminomethylphosphonate derivative, and consistent with the safety limitations of the experimental system. In a preferred embodiment, the hydrogen pressure is between about 0.25 and 5000 psi, more preferably between about 0.5 and about 3000 psi and most preferably between about 1 and about 1000 psi, for example, between about 25 and about 300 psi.

The catalyst is generally any material effective at catalyzing the formation of aminomethylphosphonate derivatives according to the inventive method. In a preferred embodiment, the catalyst is a transition metal catalyst. For example, the hydrogenation step can use a catalyst of a cobalt-containing compound, a nickel-containing compound, a platinum-containing compound, a palladium-containing compound or a rhodium-containing compound. More preferably, the catalyst is Raney cobalt, Raney nickel, a platinum promoted Raney nickel such as platinum tetrachloride ($PtCl_4$) promoted Raney nickel, platinum on carbon, palladium on carbon or rhodium on carbon. The catalyst can be used at a stoichiometric amount or catalytic amount with respect to the cyanophosphonate derivative. The stoichiometric amount is preferably between about 1 molar equivalent and about 5 molar equivalents with respect to the cyanophosphonate derivative, and more preferably between about 1 molar equivalent and about 2 molar equivalents with respect to the cyanophosphonate derivative. The catalytic amount is preferably between about 0.1 molar percent and about 100 molar percent with respect to the cyanophosphonate derivative, and more preferably between about 0.5 molar percent and about 50 molar percent with respect to the cyanophosphonate derivative.

In the event that a catalyst of platinum on carbon, palladium on carbon or rhodium on carbon is used, the hydrogenation reaction mixture preferably further contains an acid in an amount sufficient to promote formation of the desired product. The acid can be an inorganic acid or an organic acid. The inorganic acid is preferably hydrochloric acid, sulfuric acid, phosphoric acid, nitric acid or hydrocyanic acid and, more preferably, is hydrochloric acid. The organic acid is preferably acetic acid, trifluoroacetic acid, trifluoromethanesulfonic acid p-toluenesulfonic acid. The acid is preferably added to the hydrogenation reaction mixture at a concentration between about 0.1 and 5 molar equivalents with respect to the cyanophosphonate derivative, more preferably at a concentration between about 0.5 and about 2.5 molar equivalents with respect to the cyanophosphonate derivative, and most preferably at a concentration of about 1 molar equivalent or about 2 molar equivalents with respect to the cyanophosphonate derivative, depending on the degree of protonation.

In a preferred embodiment the reaction product mixture from the hydrogenation step is heated under sufficient conditions to further promote the formation of the aminomethylphosphonate derivative. For example, a product mixture that has been partially or substantially hydrogenated can be heated to a temperature in the range of about 40° C. to about 200° C, and more preferably to a range of about 80° C. to about 160° C. This heating step may be conducted for any amount of time that further promotes the aminomethylphosphonate derivative formation, preferably about 1 to about 12 hours. The heating time for optimum aminomethylphosphonate derivative formation can depend on the pH and the nature of the cations in the reaction mixture.

Representative conditions and yields are indicated below in Table I.

TABLE I

Hydrogenation of Cyanophosphonate Derivatives to Aminomethylphosphonate (AMPA)

| Cyanophosphonate Cations | Catalyst | Catalyst Weight (mg) | Substrate mmoles | Solvent | Additives | $H_2$ psi | Temperature (° C.) | AMPA Yield |
|---|---|---|---|---|---|---|---|---|
| 2 Na+ | 5% Rh/C Strem 45-1860 lot #18664-S | 138.7 | 4.87 | water | 2 eq HCl-dioxane | 1015 | 23 | 101 (HPLC) 96 (NMR) |
| 2 NH$_4$+ | 5% Rh/C Strem | 125 | 4.08 | water | 2.1 eq HCl-dioxane | 1020 | 25 | 97.9 (HPLC) 98.3 (NMR) |
| 2 Na+ | 10% Pt/C Aldrich 20595-8 03716AN | 150.5 | 5.01 | water | 2 eq HCl-dioxane | 989 | 26 | 97.8 (HPLC) 90 (NMR) |
| 2Na+ | 10% Pd/C Aldrich HZ08520DZ | 142 | 4.98 | water | 2 eq HCl-dioxane | 1010 | 25 | 86 (HPLC) |
| 2 Na+ | 10% Pt/C Aldrich 20595-8 03716AN | 149.5 | 5.01 | water | 2 eq HCl-dioxane | ~1000 | ~27 | 84.9 (HPLC) 87 (NMR) |
| 2Na+ | Raney Ni W2 50% slurry in water[a] | 528 | 5.01 | water | PtCl$_4$ 0.53 wt ratio PtCl$_4$/Ni | 512 | 24 | 71 (HPLC) 84 (NMR) |
| 2 K+ | Raney Ni W2 50% slurry in water[a] | 117.5 | 1.00 | water | PtCl$_4$ 1.78 wt ratio PtCl$_4$/Ni | 75 | 22 | 62.6 (HPLC) |
| 2 Na+ | 5% Rh/C Strem 45-1860 lot #18664-S | 138.3 | 5.01 | AcOH | | 1008 | 21 | 51 (HPLC) 57 (NMR) |
| 2 K+ | Raney Ni W2 50% slurry in water[a] | 115.1 | 1.00 | water | PtCl$_4$ 0.52 wt ratio PtCl$_4$/Ni | 75 | 22 | 51.7 (HPLC) |
| 2Na+ | 5% Pt/C Aldrich 20593-1 06709EG | 150.2 | 5.01 | water | 2.8 eq HCl-dioxane | 1013 | 26 | 49.3 (HPLC) |
| 2 Na+ | 5% Pt/C Aldrich 20593-1 06709EG | 149.2 | 5.02 | water | 2 eq HCl-dioxane | 994 | 28 | 47.4 (HPLC) |
| 2 Na+ | Raney Ni W2 weighed wet with ethanol | 127 | 1.01 | water | | 75 | 22 | 33.5 (HPLC) |
| 2 Na+ | 5% Pt/C Aldrich 20593-1 06709EG | 149.8 | 5.02 | water | 0.64 eq HCl-dioxane | 990 | 26 | 19 (HPLC) |
| 2 Na+ | Raney Co Davison, Raney 2724 w/ Ni, Cr; weighed as 50% slurry | 441 | 5.01 | water | | 1008 | 23 | 18 (HPLC) 13 (NMR) |
| 2 Na+ | PtCl$_4$ Aldrich 0.42 mmol | 141 | 5.02 | water | | 500 | 28 | 18 (HPLC) |
| 2 Na+ | 10% Pt/C Aldrich 20595-8 03716AN | 150.4 | 5.00 | water | 1 eq HCl-dioxane | 1005 | 27 | 15.0 (HPLC) |
| 2 Na+ | 10% Pt/C Aldrich 20595-8 03716AN | 30.3 | 1.00 | water | 2 eq HCl-dioxane | 75 | 24 | 10 (NMR) |

[a] = Raney Ni W2 50% slurry in water prepared as per Organic Syntheses, Collective Volume 3, pages 181–183.

Ethylcyanophosphonate Reduction to EtAMPA

| Ethylcyano-phosphonate Cations | Catalyst | Catalyst Weight (mg) | Substrate mmoles | Solvent | Additives | $H_2$ psi | Temperature (° C.) | EtAMPA Yield |
|---|---|---|---|---|---|---|---|---|
| 2 Na+ | 5% Rh/C Strem | 156 | 5.12 | water | 1 eq HCl-dioxane | 1020 | 24 | 70 (NMR) |

The products of the hydrogenation step can be isolated from the reaction mixture by conventional methods or can be used for some purposes without isolation from the reaction product mixture.

The following additional examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1
General Procedure for Low Pressure Hydrogenations (less than 100 psi)

Dipotassium cyanophosphonate (0.133 g, 1.0 mmol) was added to Raney nickel (0.118 g, as a 50% slurry in water, W2 form prepared as per *Organic Syntheses, Collective Volume 3*, pages 181–183) in a Fisher Porter bottle containing a stir bar. Water (5 mL) was added, and platinum tetrachloride (0.105 g, 0.31 mmol, Aldrich) was added. The pressure bottle was immediately connected to a hydrogen manifold, and three purges with hydrogen at 75 psi were done, and the bottle was pressurized to 75 psi. The reaction mixture was vigorously stirred for 25.5 hours at room temperature. The pressure was then released and the reaction mixture was filtered. HPLC analysis determined a 63% yield of aminomethylphosphonic acid.

Example 2
General Procedure for High Pressure Hydrogenation (500 psi or greater)

To a 300 mL Autoclave Engineers autoclave, $Na_2O_3PCN$ $(H_2O)_{0.49}$ (0.80 g, 5.0 mmol) was added, followed by 10% Pt on carbon (0.15 g, Aldrich), water (100 mL) and then HCl-dioxane (2.5 mL, 4 N, 10.0 mL). The autoclave was sealed, pressurized once with nitrogen above 500 psi, vented and pressurized with hydrogen to 1001 psi. Stirring at about 1500 rpm was then started. Within about 10 minutes, the internal pressure was about 996 psi, and the autoclave internal temperature was about 26° C. After stirring overnight, the hydrogen was vented, the autoclave was repressurized with nitrogen and vented, and then the reactor was opened and the reaction mixture removed. The reaction mixture was filtered, and the resulting solution analyzed by HPLC. The yield of aminomethylphosphonic acid determined by HPLC was 85%, and the yield by NMR was 87%.

Example 3
Reaction of $P_4O_{10}$ with $K^{13}CN$ and Triethylamine, Followed by Hydrolysis and Catalytic Hydrogenation Using 5% Rh/C and HCl to Produce AMPA In dry acetonitrile (7 mL), phosphoric anhydride (0.35 g, 1.233 mmol) was stirred with triethylamine (0.70 g, 6.9 mmol) for 10 minutes. At the end of this time, $K^{13}CN$ (0.35 g, 5.3 mmol) was added and stirring was continued for 16 hours at 25° C. The volatile components were removed under reduced pressure, and pH 2 buffer (2 mL) was added. This mixture was shaken until homogeneous, then allowed to stand for 3 days at room temperature. After this time, the solution was stored at 4° C. for 3 days. The $^{31}P$ NMR spectrum showed the presence of cyanophosphonate (30.2%) and cyano-polyphosphates (16.8%). This mixture was placed in an autoclave, after which water (100 ml) was added, followed by 5% Rh/C (Strem, 140 mg), then HCl-dioxane (4N, 2.5 mL, 10 mmol). The autoclave was then sealed, purged once with nitrogen, and pressurized with hydrogen to 1000 psi. The reaction was stirred overnight (19 hours). At the end of this time, the hydrogen pressure was released, the autoclave was pressurized once with nitrogen, the pressure was released and the autoclave was opened. The collected reaction mixture was filtered, stirred with Chelex resin, filtered again and analyzed by HPLC (phosphate detection method). The yield of AMPA was 32.6% by HPLC, based on phosphorus equivalents charged as phosphoric anhydride. The $^{31}P$ NMR was consistent with this formulation. It is expected that the AMPA yield in this product solution will increase with further treatment, for example, with the addition of a suitable amount of acid or base and appropriate heating.

Example 4
Conversion of Phosphoric Anhydride to AMPA

Phosphoric anhydride was treated with potassium cyanide and amine following the procedure No. 6 using about 1.25 mmol of phosphoric anhydride. At the end of this reaction, the solvent was removed under reduced pressure. For the 1 h hydrolyses, the resulting powder was added to water (100 mL) in an autoclave containing hydrogen chloride-dioxane (10 mmol) and 5% Rh/C (122 to 139 milligrams), and was hydrogenated at about 1000 psi overnight at room temperature following the procedure No. 8. For the 2 and 3 day hydrolyses, hydrolysis took place at room temperature, then, the hydrolysis mixture was kept at the indicated temperature for the rest of the hydrolysis time. The hydrogenation was then performed as for the short hydrolysis time experiments. After the pressure was released and the system purged with nitrogen, the reaction mixture was filtered, and the amount of AMPA was determined by HPLC. The reaction mixtures were then heated to the temperature specified below for the period of time indicated, and the amount of AMPA was determined. In the following Table II, the hydrolysis time refers to the duration of the hydrolysis prior to the start of the hydrogenation; n.d. indicates that a yield was not determined.

TABLE II

Reaction Conditions and Yield for Conversion of $P_4O_{10}$ to AMPA

| $P_4O_{10}$ Expt. | Amine | Hydrolysis Time | Yield $O_3PCN$ | Yield Cyanopoly-phosphates | AMPA Yield, no heating | AMPA Yield, with heating | Temp ° C. | Time |
|---|---|---|---|---|---|---|---|---|
| 1 | NEt$_3$ | 3 days, rt | 30% | 17% | 33% | 38% | 85 | 4 h |
|  |  |  |  |  |  | 46% | 85 | 1 day |
| 2 | t-BuPyr | 1 h, rt | 10% | 61% | 32% | 56% | 85 | 1 day |
|  |  | 2 days, rt, then 4° C. | 38% | 29% | 44% | 57% | 85 | 1 day |

TABLE II-continued

Reaction Conditions and Yield for Conversion of $P_4O_{10}$ to AMPA

| $P_4O_{10}$ Expt. | Amine | Hydrolysis Time | Yield $O_3PCN$ | Yield Cyanopoly-phosphates | AMPA Yield, no heating | AMPA Yield, with heating | Temp °C. | Time |
|---|---|---|---|---|---|---|---|---|
| 3 | t-BuPyr | 1 h, rt | n.d. | n.d. | 21% | 66% | 118 | 2 h |
|  |  |  |  |  |  | 73% | 118 | 4.5 h |

All of the compositions and methods disclosed and claimed herein can be made and executed without undue experimentation in light of the present disclosure. While the compositions and methods of this invention have been described in terms of preferred embodiments, it will be apparent to those of skill in the art that variations can be applied to the process described herein without departing from the concept, spirit and scope of the invention. All such similar substitutes and modifications apparent to those skilled in the art are deemed to be within the spirit, scope and concept of the invention.

What is claimed is:

1. A method for preparing an aminomethylphosphonate derivative comprising:

contacting a cyanophosphonate derivative, hydrogen and a suitable catalyst in a reaction mixture under sufficient conditions to produce an aminomethylphosphonate derivative.

2. The method of claim 1, wherein the cyanophosphonate derivative is a cyanophosphonate disalt, a cyanophosphonate monosalt monoester, a cyanophosphonate diester, a cyanophosphonate monosalt monoacid, a cyanophosphonate monoacid monoester or cyanophosphonic acid.

3. The method of claim 1, wherein the cyanophosphonate derivative is a cyclic cyanophosphonate anhydride, a linear or polymeric cyanophosphonate anhydride, a mixed linear or polymeric cyanophosphonate-phosphate anhydride, a mixed linear or polymeric cyclic cyanophosphonate-phosphate anhydride or a mixed cyclic cyanophosphonate-phosphate anhydride.

4. The method of claim 2, wherein the cyanophosphonate derivative is disodium cyanophosphonate, dipotassium cyanophosphonate, dilithium cyanophosphonate, bis(2-hydroxyethylammonium)cyanophosphonate, bis(ammonium)cyanophosphonate, bis-(isopropylammonium) cyanophosphonate, mono(isopropylammonium) cyanophosphonate bis(dimethylammonium) cyanophosphonate, bis(trimethylsulfonium) cyanophosphonate, bis(dicyclohexylammonium) cyanophosphonate, cyanophosphonic acid, sodium hydrogen cyanophosphonate, potassium hydrogen cyanophosphonate, lithium hydrogen cyanophosphonate, methyl cyanophosphonic acid, ethyl cyanophosphonic acid, sodium methyl cyanophosphonate, sodium ethyl cyanophosphonate, potassium methyl cyanophosphonate, potassium ethyl cyanophosphonate, lithium methyl cyanophosphonate, lithium ethyl cyanophosphonate, dimethylcyanophosphonate or diethylcyanophosphonate.

5. The method of claim 3, wherein the cyanophosphonate derivative is a monocyanopyrophosphate, dicyanopyrophosphate, dicyanotripolyphosphate, dicyanotetrapolyphosphate, monocyanotetrapolyphosphate, monocyanopentapolyphosphate, cyanophosphate cyclotrimer or cyanophosphate cyclotetramer.

6. The method of claim 1, wherein the reaction mixture further comprises a solvent.

7. The method of claim 6, wherein the solvent is water, acetic acid, an alcohol, dimethylacetamide, an anhydride, an amide, sulfolane or mixtures thereof.

8. The method of claim 1, wherein the catalyst is a cobalt-containing compound, a nickel-containing compound, a platinum-containing compound, a palladium-containing compound or a rhodium containing compound.

9. The method of claim 8, wherein the catalyst is Raney cobalt, Raney nickel, platinum promoted Raney nickel, platinum on carbon, palladium on carbon or rhodium on carbon.

10. The method of claim 9, wherein the catalyst is a Raney cobalt catalyst.

11. The method of claim 9, wherein the catalyst is a Raney nickel catalyst.

12. The method of claim 9, wherein the catalyst is a platinum promoted Raney nickel catalyst.

13. The method of claim 12, wherein the catalyst is a platinum tetrachloride promoted Raney nickel catalyst.

14. The method of claim 9, wherein the catalyst is palladium on carbon, platinum on carbon or rhodium on carbon.

15. The method of claim 14, wherein the reaction mixture further contains an acid.

16. The method of claim 15, wherein the acid is an inorganic acid or an organic acid.

17. The method of claim 16, wherein the inorganic acid is hydrochloric acid, phosphoric acid, nitric acid, sulfuric acid or hydrocyanic acid.

18. The method of claim 17, wherein the inorganic acid is hydrochloric acid.

19. The method of claim 16, wherein the organic acid is acetic acid, trifluoroacetic acid, trifluoromethanesulfonic acid p-toluenesulfonic acid.

20. The method of claim 16, wherein the acid is present at a concentration of between about 0.1 and about 5 molar equivalents with respect to the cyanophosphonate derivative.

21. The method of claim 20, wherein the acid is present at concentration of between about 0.5 and about 2.5 molar equivalents with respect to the cyanophosphonate derivative.

22. The method of claim 1, wherein the catalyst is present in a stoichiometric amount with respect to the cyanophosphonate derivative.

23. The method of claim 1, wherein the catalyst is present in a catalytic amount with respect to the cyanophosphonate derivative.

24. The method of claim 23, wherein the catalyst is present in a catalytic amount in the range of about 0.1 molar percent and about 100 molar percent with respect to the cyanophosphonate derivative.

25. The method of claim 24, wherein the catalyst is present in a catalytic amount in the range of about 0.5 molar percent and about 50 molar percent with respect to the cyanophosphonate derivative.

26. The method of claim 25, wherein the catalyst is present in an amount in the range of about 1 molar equivalent and 5 molar equivalents with respect to the cyanophosphonate derivative.

27. The method of claim 1, wherein the hydrogen is present at a pressure between about 0.25 and about 5000 psi.

28. The method of claim 27, wherein the hydrogen is present at a pressure between about 0.5 and about 3000 psi.

29. The method of claim 22, wherein the hydrogen is present at a pressure between about 1 and about 1000 psi.

30. The method of claim 23, wherein the hydrogen is present at a pressure between about 25 and about 300 psi.

31. The method of claim 1, wherein the temperature of the reaction mixture is between about 10° C. and about 70° C.

32. The method of claim 25, wherein the temperature of the reaction mixture is between about 20° C. and about 50° C.

33. The method of claim 26, wherein the temperature of the reaction mixture is between about 20° C. and about 40° C.

34. The method of claim 1, wherein the hydrogenation step is performed for between about 0.1 and about 24 hours.

35. The method of claim 28, wherein the hydrogenation step is performed for between about 0.1 and about 12 hours.

36. The method of claim 1, further comprising heating the hydrogenated reaction mixture under sufficient conditions to promote the formation of the aminomethylphosphonate derivative.

37. The method of claim 36, wherein the hydrogenated reaction mixture is heated to about 40° C. to about 200° C.

38. The method of claim 37, wherein the hydrogenated reaction mixture is heated to about 80° C. to about 200° C. for about 1 to about 12 hours.

39. The method of claim 37, wherein the hydrogenated reaction mixture is heated to about 135° C. to about 160° C. for about 1 to about 12 hours.

40. The method of claim 1, wherein the aminomethylphosphonate derivative is aminomethylphosphonic acid, a monoester of aminomethylphosphonic acid, a diester of aminomethylphosphonic acid, a monosalt of aminomethylphosphonic acid, a disalt of aminomethylphosphoric acid, an anhydride of aminomethylphosphonic acid, an anhydride of aminomethylphosphonic acid and phosphoric acid, a polyanhydride of aminomethylphosphonic acid, a cyclic polyanhydride of aminomethylphosphonic acid or a polyanhydride of aminomethylphosphonic acid and phosphoric acid.

41. The method of claim 40, wherein the aminomethylphosphate derivative is aminomethylphosphonic acid.

42. The method of claim 40, wherein the aminomethylphosphate derivative is ethylaminomethylphosphonate.

* * * * *